United States Patent
Boyer et al.

(10) Patent No.: US 10,597,496 B2
(45) Date of Patent: Mar. 24, 2020

(54) PLATINUM (II) DIENE COMPLEXES FOR CONTROLLED SILOXANE CROSSLINKING

(71) Applicant: Momentive Performance Materials Inc., Waterford, NY (US)

(72) Inventors: Julie Boyer, Watervliet, NY (US); Aroop Roy, Mechanicville, NY (US); David Jenkins, Cohoes, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 15/502,325

(22) PCT Filed: Sep. 18, 2015

(86) PCT No.: PCT/US2015/050954
§ 371 (c)(1),
(2) Date: Feb. 7, 2017

(87) PCT Pub. No.: WO2016/044732
PCT Pub. Date: Mar. 24, 2016

(65) Prior Publication Data
US 2017/0226293 A1 Aug. 10, 2017

Related U.S. Application Data

(60) Provisional application No. 62/052,727, filed on Sep. 19, 2014.

(51) Int. Cl.
*C08G 77/08* (2006.01)
*B01J 31/22* (2006.01)
*C08G 77/12* (2006.01)
*C08G 77/20* (2006.01)
*C08L 83/04* (2006.01)
*C07F 15/00* (2006.01)
*C09D 183/04* (2006.01)
*C07F 7/08* (2006.01)
*C08K 5/56* (2006.01)
*C08L 83/00* (2006.01)

(52) U.S. Cl.
CPC .......... *C08G 77/08* (2013.01); *B01J 31/2291* (2013.01); *C07F 7/087* (2013.01); *C07F 15/0086* (2013.01); *C08G 77/12* (2013.01); *C08G 77/20* (2013.01); *C08K 5/56* (2013.01); *C08L 83/00* (2013.01); *C08L 83/04* (2013.01); *C09D 183/04* (2013.01); *B01J 2231/323* (2013.01); *B01J 2531/828* (2013.01)

(58) Field of Classification Search
CPC .......... B01J 23/40; C08G 77/12; C08G 77/20
See application file for complete search history.

(56) References Cited

U.S. PATENT DOCUMENTS

| | | | | | |
|---|---|---|---|---|---|
| 3,933,880 | A | * | 1/1976 | Bergstrom | C07F 7/0879 556/449 |
| 5,357,007 | A | * | 10/1994 | Wengrovius | C08L 83/04 525/478 |
| 5,561,231 | A | | 10/1996 | Dauth et al. | |
| 7,511,110 | B2 | * | 3/2009 | Fehn | B01J 31/185 502/150 |
| 8,075,307 | B2 | | 12/2011 | Jessop et al. | |
| 2004/0254274 | A1 | | 12/2004 | Griswold | |
| 2013/0171265 | A1 | | 7/2013 | Saxena et al. | |
| 2016/0030932 | A1 | * | 2/2016 | Choi | C01B 33/20 423/700 |
| 2016/0135689 | A1 | | 5/2016 | Murakoshi | |

FOREIGN PATENT DOCUMENTS

| | | |
|---|---|---|
| CA | 2895660 A1 | 6/2014 |
| CN | 1809619 A | 7/2006 |
| EP | 0472438 | 2/1992 |
| EP | 0994159 | 4/2000 |
| JP | 54076529 | 6/1979 |
| JP | 54076530 | 6/1979 |
| WO | 9210529 | 6/1992 |
| WO | 2007092118 A2 | 8/2007 |
| WO | 2012016925 A2 | 2/2012 |
| WO | 2013158272 A1 | 10/2013 |
| WO | 2014142252 * | 9/2014 |

OTHER PUBLICATIONS

Boyer et al., "Redox Activation of Alkene Ligands in Platinum Complexes with Non-innocent Ligands," Inorganic Chemistry, vol. 48, No. 2. pp. 638-645. (2009).
Liu, WP et al., "Novel Lipophilic Platinum(II) Compounds of Salicylate Derivatives," Platinum Metals Rev., vol. 52, No. 3, pp. 163-171. (2008).
Gietema, JA et al., "A phase I study of 1,2-diamminomethyl-cyclobutane-platinum (II)-lactate (D-19466; lobaplatin) administered daily for 5 days," Br. J. Cancer, vol. 67, pp. 396-401. (1993).
Patent Cooperation Treaty (PCT), International Search Report and Written Opinion for Application PCT/US2015/050954 filed Sep. 18, 2015, dated Dec. 23, 2015, International Searching Authority, US.
Lewis et al., "Platinum-catalyzed hydrosilylation of alkynes," Organometallics, vol. 10, No. 10, pp. 3750-3759. (1991).
Casei et al., "Hydrosilylation chemistry and catalysis with cis-PtCl2(PhCH:CH2)2," Organometallics, vol. 7, No. 6, pp. 1373-1380. (1988).
Don et al., "Synthesis, redox properties, and X-ray diffraction structure of the platinum catecholate complex Pt(1,5-COD)(1,2-O2C6H4)," Journal of Chemical Crystallography, Col. 26, Issue 5, pp. 335-340. (1996).

* cited by examiner

*Primary Examiner* — Kuo Liang Peng
(74) *Attorney, Agent, or Firm* — Joseph Waters; McDonald Hopkins LLC

(57) ABSTRACT

A process for cross-linking siloxane and organic polymers comprising reacting (a) a silyl hydride with (b) an unsaturated polymeric compound in the presence of (d) a platinum diene compound with a chelating dianionic ligand.

41 Claims, No Drawings

PLATINUM (II) DIENE COMPLEXES FOR CONTROLLED SILOXANE CROSSLINKING

CROSS-REFERENCE TO RELATED APPLICATIONS

This application claims priority to and the benefit of International Patent Application No. PCT/US2015/050954 titled "Platinum (II) Diene Complexes for Controlled Siloxane Crosslinking," filed on Sep. 18, 2015, which claims priority to and the benefit of U.S. Provisional Application No. 62/052,727 titled "Platinum (II) Diene Complexes for Controlled Siloxane Crosslinking" filed on Sep. 19, 2014, the disclosure of each of which is incorporated by reference herein in its entirety.

FIELD OF THE INVENTION

The present invention relates generally to the use of platinum (II) diene complexes with chelating anions to catalyze siloxane crosslinking reactions.

BACKGROUND

Hydrosilylation chemistry, involving the reaction between a silylhydride and an unsaturated organic group, is the basis for many addition cured products including sealants, elastomers, RTVs, adhesives, and silicone-based coatings. Addition cured silicone formulations are typically comprised of:
  (A) an alkenyl substituted polysiloxane that is the primary component or base polymer of the curable composition;
  (B) a hydride functional crosslinking silicone, typically a methyl hydrogen siloxane polymer, copolymer or oligomer;
  (C) a highly active addition cure hydrosilylation catalyst, typically a platinum (0) catalyst such as Ashby's or Karstedt's; and
  (D) a cure inhibiting compound or mixtures thereof to increase the useful life of the complete formulation.

Addition curable silicone formulations of the above composition must have both rapid cure at elevated temperature and an acceptably long working life (i.e., no crosslinking) of the full formulation at room temperature. This need is particularly acute for release coating formulations where perhaps the most stringent demand is placed on the catalyst for extremely fast cure at high line coating speeds and very short oven-dwell times (2-5 seconds), together with good bath life of the formulation. Yet, the formulation must essentially completely cure in seconds at elevated temperature to meet release performance requirements on a plethora of different paper and polymeric substrates. To accommodate these two opposing demands, two part formulations with high platinum loadings and high inhibitor loadings are typically employed in the industry. This current solution has several distinct disadvantages. High platinum catalyst loadings are required in addition curable systems to ensure rapid and complete cure at elevated temperature but this high loading of precious metal catalysts also imparts a significant catalyst cost to the formulation. In addition to cure performance, high platinum catalyst levels are especially needed in release liner applications to ensure adequate anchorage to the substrate. High levels of inhibitors are employed to retard catalyst activity and to extend working life of the formulation at room temperature, but the inhibitors employed may not be rapidly de-complexed from the platinum center at elevated temperature and slow the desired crosslinking reaction at elevated temperature. Lastly, two part formulations require additional time and mixing steps before the use of the formulation.

Other platinum based catalysts besides the previously mentioned Karstedt's and Ashby's catalysts have been reported. PtCODCl$_2$, PtCODMe$_2$, and PtCODPh$_2$ are commercially available and their use as catalysts for hydrosilylation reactions has been known for many years (JP 54076530A, JP 54076529A, EP 472438, L. Lewis et al., Organometallics, 1991, 10, 3750-3759, and P. Pregosin et al., Organometallics, 1988, 7, 1373-1380). Roy et al. have reported the preparation of a series of PtCOD(SiR$_3$)$_2$ compounds from PtCODCl$_2$ (Roy, Aroop K.; Taylor, Richard B. J. Am Chem. Soc., 2012, 124, 9510-9524; and U.S. Pat. No. 6,605,734), but their use in silicone crosslinking is not reported or indicated. The use of PtCODPh$_2$ has been reported for use in radiation cure systems (WO9210529). Complexes with the general formula PtCOD(alkynyl)$_2$ and Pt(COD)(ureylene) have been cited as catalysts in curable silicone rubber compositions (EP 0994159, U.S. Pat. No. 7,511,110). These complexes, however, suffer from their poor solubility in organic solution and silicone formulations. Chlorinated solvents such as chloroform or dichloromethane are employed to dissolve the catalyst. In addition to health and environmental concerns posed by such chlorinated solvents, they are also highly volatile which poses formulation challenges.

Pt-COD complexes with catecholate or amidophenolate ligands have been reported (Boyer et al. Inorg. Chem 2009, 48, 638-645; Richmond et al, J. Chem. Crystallogr. 1996, 26, 335-340). These papers describe the electronic structure and redox reactivity of these Pt complexes. The use of these platinum-diene complexes with chelating dianions in hydrosilylation reactions has not been reported.

There is a need in the silicone industry for platinum catalysts of improved stability as industry work-horse catalysts such as Speier's and Karstedt's are prone to partial deactivation via agglomeration, especially at elevated temperatures of use. Improved stability of the active catalyst would enable the lowering of Pt catalyst loadings. In addition to improved stability, catalysts that demonstrate rapid activation and high hydrosilylation activity at elevated temperature, but also display a long working life for formulations stored at room temperature at low or no inhibitor loadings are especially sought. Lastly, platinum catalysts are needed that have improved solubility in industrially-preferred organic solvent or silicones. The present invention provides one solution to these needs.

SUMMARY

The present invention provides the use of platinum-diene complexes with chelating dianionic ligands in hydrosilylation reactions. It has been found that platinum-diene complexes with chelating dianionic ligands are suitable for use in crosslinking reactions and exhibit acceptable to very good activity at low platinum loadings and low inhibitor loadings. The new catalysts show desirable catalysis improvements such as reduced level of Pt use, longer working life with no or less inhibitor, rapid cure and improved anchorage to substrates at elevated temperature, and improved solubility in organics and silicone formulations.

The present invention provides, in one aspect, a process for producing a crosslinked product comprising reacting (a) an alkenyl silicone, (b) a hydrogen siloxane, (c) optionally a cure inhibitor, and (d) a catalyst, optionally in the presence of a solvent, wherein the catalyst comprises a compound of the formula:

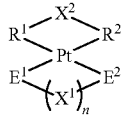

Formula (I)

wherein $R^1$—$X^2$—$R^2$ is a diene that is bonded to platinum in an $\eta^4$-mode and is a branched chain, an unbranched chain, a cyclic system, or a bicyclic system having 4 to 30 carbon atoms;

$E^1$ and $E^2$ are independently chosen from monoanionic ligands of O, $NR^3$, a carboxyl group [C(O)O], or S;

$R^3$ is independently hydrogen, or a monovalent hydrocarbon radical having from 1 to 30 carbon atoms;

$X^1$ is a divalent hydrocarbyl or silicone group such as substituted or unsubstituted alkylene, arylene, or siloxanylene group with the proviso that the $E^1$-$X^1$-$E^2$ ligand of Formula (I) does not include ureylene or alpha hydroxy acid ligands;

$X^2$ is a divalent hydrocarbyl such as substituted or unsubstituted alkylene, arylene, or cycloalkylene group, whereby the bonding olefin moieties are terminal and/or internal and $X^2$ represents bridges between the olefinic groups; and n is 0, 1, 2, 3, or 4.

In one embodiment of the process, $E^1$ and $E^2$ are O.

The process of any previous embodiment, wherein $R^1$—$X^2$—$R^2$ is chosen from 1,5-cyclooctadiene, norbornadiene, dicyclopentadiene, or 1,5-hexadiene.

The process of any previous embodiment, wherein $E^1$-$X^1$-$E^2$ is chosen from amidophenolate, phenylenediamide, benzenedithiolate, mercaptophenolate, mercaptoethanolate, pinacolate, ethylene diolate, propandiolate, catecholate, substituted catecholate, salicylate, oxalate, or malonate.

The process of any previous embodiment, wherein $R^1$—$X^2$—$R^2$ is 1,5-cyclooctadiene.

The process of any previous embodiment, wherein $E^1$-$X^1$-$E^2$ is pinacolate, and $R^1$—$X^2$—$R^2$ is 1,5-cyclooctadiene.

The process of any previous embodiment, wherein $E^1$-$X^1$-$E^2$ is represented by the formula:

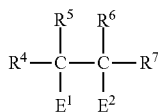

where $R^4$, $R^5$, $R^6$, and $R^7$ are independently chosen from hydrogen, a C1-C20 alkyl, and a C6-C10 aryl.

The process of any previous embodiment, wherein $E^1$-$X^1$-$E^2$ is represented by the formula:

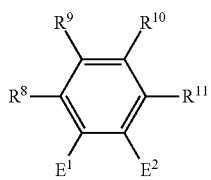

where $R^8$, $R^9$, $R^{10}$, and $R^{11}$ are independently chosen from hydrogen and a C1-C20 alkyl. In one embodiment, $R^8$, $R^9$, $R^{10}$, and $R^{11}$ are each hydrogen. In one embodiment, $R^8$ and $R^{10}$ are independently chosen from a C1-C20 alkyl, and $R^9$ and $R^{11}$ are each hydrogen. In one embodiment, $R^8$ and $R^{10}$ are each tert-butyl.

The process of any previous embodiment, wherein $E^1$ and $E^2$ are each O.

The process of any previous embodiment, wherein $E^1$ and $E^2$ are independently chosen from O and S.

The process of any previous embodiment, wherein the curable alkenyl silicone is of the formula:

wherein $M^{vi}_a = R^{12}_2 R^{13} SiO_{1/2}$; $T_b = R^{14} SiO_{3/2}$ where $R^{14}$ is chosen from $R^{12}$ or $R^{13}$; $D_c = R^{12} R^{14} SiO_{2/2}$ where $R^{14}$ is chosen from $R^{12}$ or $R^{13}$; $M_d = R^{12}_3 SiO_{1/2}$; and $Q_e = SiO_{4/2}$; $R^{12}$ is independently selected from a monovalent hydrocarbon radical having one to forty carbon, optionally containing at least one heteroatom; and $R^{13}$ is selected from a terminal olefinic monovalent hydrocarbon radical having two to forty carbon atoms, optionally containing at least one heteroatom, where the composition of the alkenyl silicone comprises at least two unsaturated groups reactive to hydrosilylation per chain; a≥0, b≥0, d≥0, e≥0; values for c in particular are determined by the desired properties and attributes of the cross-linked material so that the sum a+b+c+d+e is in the range 50-20,000.

The process of any previous embodiment, wherein the hydrogen siloxane is chosen from a compound of the formula $M_{a'} M^H_{b'} D_{c'} D^H_{d'} T_{e'} T^H_{f'} Q_{g'}$, where the subscripts a', b', c', d', e', f, and g are such that the molar mass of the siloxane-type reactant is between 100 and 100,000 Dalton; M is a monofunctional group of formula $R^{15}_3 SiO_{1/2}$, D is a difunctional group of formula $R^{15}_2 SiO_{2/2}$, T is a trifunctional group of formula $R^{15} SiO_{3/2}$, and Q is a tetrafunctional group of formula $SiO_{4/2}$, $M^H$ is $HR^{15}_2 SiO_{1/2}$, $T^H$ is $HSiO_{3/2}$, and $D^H$ is $R^{15} HSiO_{2/2}$, where each occurrence of $R^7$ is independently chosen from a C1-C40 alkyl, a C1-C40 substituted alkyl, a C6-C14 aryl or substituted aryl, wherein $R^{15}$ optionally contains at least one heteroatom.

The process of any previous embodiment, wherein the inhibitor is chosen from ethylenically unsaturated amides, aromatically unsaturated amides, acetylenic compounds, ethylenically unsaturated isocyanates, olefinic siloxanes, unsaturated hydrocarbon diesters, unsaturated hydrocarbon mono-esters of unsaturated acids, conjugated or isolated ene-ynes, hydroperoxides, ketones, sulfoxides, amine, phosphines, phosphites, nitrites, diaziridines, or a combination of two or more thereof.

The process of any previous embodiment, wherein the concentration of platinum is from about 100 parts per billion (ppb) to about 100 ppm.

The process of any previous embodiment, wherein component (c) is present in an amount of from about 0 to about 10 weight percent.

The process of any previous embodiment, wherein components (a)-(d) are provided in a single composition.

The process of any previous embodiment, wherein the reaction is completed in about 10 seconds or less.

The process of any previous embodiment, wherein the reaction is completed in 2-5 seconds.

The process of any previous embodiment, wherein the process is conducted by heating at a temperature above room temperature.

The process of any previous embodiment, wherein the a composition of components (a)-(d) has a working life of at least 2 hours when the concentration of inhibitor (c) is about 0.25 weight percent or less.

In another aspect, the present invention provides a composition comprising (a) an alkenyl silicone, (b) a hydrogen siloxane, (c) optionally a cure inhibitor, and (d) a catalyst, optionally in the presence of a solvent, wherein the catalyst comprises a compound of the formula:

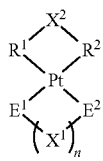

Formula (I)

wherein $R^1$—$X^2$—$R^2$ is a diene that is bonded to platinum in $\eta^4$-mode and is a branched chain, an unbranched chain, a cyclic system, or a bicyclic system having 4 to 30 carbon atoms;
$E^1$ and $E^2$ are independently chosen from monoanionic ligands of O, $NR^3$, a carboxyl group [C(O)O], or S;
$R^3$ are each independently hydrogen, or a monovalent hydrocarbon radical having from 1 to 30 carbon atoms;
$X^1$ is a divalent hydrocarbyl or silicone group such as substituted or unsubstituted alkylene, arylene, or siloxanylene group with the proviso that the $E^1$-$X^1$-$E^2$ ligand of Formula (I) does not include urelyene or alpha hydroxy acid ligands;
$X^2$ is a divalent hydrocarbyl such as substituted or unsubstituted alkylene, arylene, or cycloalkylene group, whereby the bonding olefin moieties are terminal and/or internal and $X^2$ represents bridges between the olefinic groups; and
n is 0, 1, 2, 3, or 4.

In one embodiment of the composition, $E^1$ and $E^2$ are O.

The composition of any previous embodiment, wherein $R^1$—$X^2$—$R^2$ is chosen from 1,5-cyclooctadiene, norbornadiene, dicyclopentadiene, or 1,5-hexadiene.

The composition of any previous embodiment, wherein $E^1$-$X^1$-$E^2$ is chosen from amidophenolate, phenylenediamide, benzenedithiolate, mercaptophenolate, mercaptoethanolate, pinacolate, ethanediolate, propanediolate, catecholate, substituted catecholate, salicylate, oxalate, or malonate.

The composition of any previous embodiment, wherein $R^1$—$X^2$—$R^2$ is 1,5-cyclooctadiene.

The composition of any previous embodiment, wherein the catalyst (c) is chosen from pinacolate-Pt-cycloooctadiene; propanediolate-Pt-cyclooctadiene; salicylate-Pt-cyclooctadiene, or a combination of two or more thereof.

The composition of any previous embodiment, wherein the curable alkenyl silicone is of the formula:

$M^{vi}{}_a T_b D_c M_d Q_e$ wherein $M^{vi}{}_a = R^{12}{}_2 R^{13} SiO_{1/2}$; $T_b = R^{14} SiO_{3/2}$ where $R^{14}$ is chosen from $R^{12}$ or $R^{13}$; $D_c = R^{12} R^{14} SiO_{2/2}$ where $R^{14}$ is chosen from $R^{12}$ or $R^{13}$; $M_d = R^{12}{}_3 SiO_{1/2}$; and $Q_e = SiO_{4/2}$; $R^{12}$ is independently selected from a monovalent hydrocarbon radical having one to forty carbon, optionally containing at least one heteroatom; and $R^{13}$ is selected from a terminal olefinic monovalent hydrocarbon radical having two to forty carbon atoms, optionally containing at least one heteroatom, where the alkenyl silicone comprises at least two unsaturated groups reactive to hydrosilylation per chain; a≥0, b≥0, d≥0, e≥0; values for c in particular are determined by the desired properties and attributes of the cross-linked material so that the sum a+b+c+d+e is in the range 50-20,000.

The composition of any previous embodiment, wherein the hydrogen siloxane is chosen from a compound of the formula $M_{a'} M^H{}_{b'} D_{c'} D^H{}_{d'} T_{e'} T^H{}_{f} Q_{g}$, where the subscripts a', b', c', d', e', f, and g are such that the molar mass of the siloxane-type reactant is between 100 and 100,000 Dalton; M is a monofunctional group of formula $R^{15}{}_3 SiO_{1/2}$, D is a difunctional group of formula $R^{15}{}_2 SiO_{2/2}$, T is a trifunctional group of formula $R^{15} SiO_{3/2}$, and Q is a tetrafunctional group of formula $SiO_{4/2}$, $M^H$ is $HR^{15}{}_2 SiO_{1/2}$, $T^H$ is $HSiO_{3/2}$, and $D^H$ is $R^{15} HSiO_{2/2}$, and each occurrence of $R^{15}$ is independently chosen from a C1-C40 alkyl, a C1-C40 substituted alkyl, a C6-C14 aryl or substituted aryl, wherein $R^{15}$ optionally contains at least one heteroatom.

The composition of any previous embodiment, wherein the inhibitor is chosen from ethylenically unsaturated amides, aromatically unsaturated amides, acetylenic compounds, ethylenically unsaturated isocyanates, olefinic siloxanes, unsaturated hydrocarbon diesters, unsaturated hydrocarbon mono-esters of unsaturated acids, conjugated or isolated ene-ynes, hydroperoxides, ketones, sulfoxides, amine, phosphines, phosphites, nitrites, diaziridines, or a combination of two or more thereof.

The composition of any previous embodiment, wherein the concentration of platinum is from about 100 parts per billion (ppb) to about 100 ppm.

The composition of any previous embodiment, wherein components (a)-(d) are a single component composition.

In another aspect, the present invention provides a cured material prepared from the composition of any of the previous embodiments. In one embodiment, the cured material comprises the catalyst component (d).

In still another aspect, the present invention provides a coating formed from the composition of any the previous embodiments. The present invention also provides a substrate having a surface thereof at least partially coated with such coatings. In embodiments, the coating is anchored to the surface of the substrate.

In yet another aspect, the present invention provides a compound of the formula:

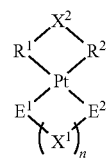

Formula (I)

wherein $R^1$—$X^2$—$R^2$ is a diene that is bonded to platinum in an $\eta^4$-mode and is a branched chain, an unbranched chain, a cyclic system, or a bicyclic system having 4 to 30 carbon atoms; $E^1$-$X^1$-$E^2$ is chosen from mercaptophenolate, pinacolate, propanediolate, or salicylate; and $X^2$ is a divalent hydrocarbyl such as substituted or unsubstituted alkylene, arylene, or cycloalkylene group, whereby the bonding olefin moieties are terminal and/or internal and $X^2$ represents bridges between the olefinic groups.

In one embodiment of the compound, $R^1$—$X^2$—$R^2$ is chosen from 1,5-cyclooctadiene, norbornadiene, dicyclopentadiene, or 1,5-hexadiene.

The compound of any previous embodiment, wherein the compound is chosen from pinacolate-Pt-cyclooctadiene; propanediolate-Pt-cyclooctadiene; or salicylate-Pt-cyclooctadiene.

In a further aspect, the present invention provides a process for producing a crosslinked product comprising reacting (a) an alkenyl silicone, (b) a hydrogen siloxane, (c) a cure inhibitor, and (d) a catalyst, optionally in the presence of a solvent, wherein the catalyst comprises a compound of the formula:

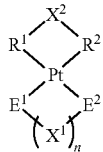

Formula (I)

wherein $R^1$—$X^2$—$R^2$ is a diene that is bonded to platinum in an $\eta^4$-mode and is a branched chain, an unbranched chain, a cyclic system, or a bicyclic system having 4 to 30 carbon atoms;
$R^3$ are each independently hydrogen, or a monovalent hydrocarbon radical having from 1 to 30 carbon atoms;
$E^1$-$X^1$-$E^2$ is an alpha hydroxy acid ligands;
$X^2$ is a divalent hydrocarbyl such as substituted or unsubstituted alkylene, arylene, or cycloalkylene group, whereby the bonding olefin moieties are internal and $X^2$ represents bridges between the olefinic groups; and
n is 0, 1, 2, 3, or 4.

In embodiments of the process, the reaction occurs in about 10 seconds or less.

The following description discloses various illustrative aspects. Some improvements and novel aspects may be expressly identified, while others may be apparent from the description.

DETAILED DESCRIPTION

In one aspect, the present invention is directed to a process for producing a crosslinked product comprising reacting a mixture comprising (a) an alkenyl silicone, (b) a hydrogen siloxane, (c) a cure inhibitor and (d) a hydrosilylation catalyst, optionally in the presence of a solvent, in order to produce the crosslinked product. In one embodiment, the catalyst is a complex of the Formula (I) or an adduct thereof;

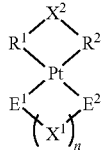

Formula (I)

where $R^1$—$X^2$—$R^2$ is a diene that is bonded to platinum in an $\eta^4$-mode and is a branched or unbranched chain, a cyclic or bicyclic system having 4 to 30 carbon atoms;
$E^1$ and $E^2$ are independently monoanionic O, $NR^3$, carboxyl group [C(O)O] or S;
$R^3$ are each independently hydrogen, or a monovalent hydrocarbon radical having from 1 to 30 carbon atoms;
$X^1$ is a divalent hydrocarbyl or silicone group such as substituted or unsubstituted alkylene, arylene, or siloxanylene group with the proviso that the $E^1$-$X^1$-$E^2$ ligand of formula one does not include urelyene or alpha hydroxy acid ligands;

$X^2$ is a divalent hydrocarbyl group such as substituted or unsubstituted alkylene, arylene, or cycloalkylene group, whereby the bonding olefin moieties are terminal and/or internal and $X^2$ represents one or more bridges between the olefinic groups; and
n is 0, 1, 2, 3, or 4.

A wide variety of chelating $E^1$-$X^1$-$E^2$ ligands can be employed as co-ligands in Pt (II) diene cure catalysts. Not to be bound by any particular theory or mechanism, desirable $E^1$-$X^1$-$E^2$ ligands would impart good solubility to the platinum catalyst in silicone formulations or organic solvent and the chelating ligand would be rapidly de-complexed/eliminated at elevated temperature (in the presence of a silylhydride). The chelating $E^1$-$X^1$-$E^2$ ligand can be varied to alter catalyst activation temperature and catalyst activation rate. Chelating $E^1$-$X^1$-$E^2$ ligands useful in this invention include amidos, thiolates, alkoxides, carboxylates or ligands containing one or more of these functional groups.

Examples of suitable dianionic chelating ligands include, but are not limited to, amidophenolate, phenylenediamide, benzenedithiolate, mercaptophenolate, mercaptoethanolate, pinacolate, ethanediolate, propanediolate, catecholate, substituted catecholates, salicylate, oxalate, malonate, N,O-dianions of amino acids, etc.

In embodiments, the dianionic chelating ligand $E^1$-$X^1$-$E^2$ is represented by the formula:

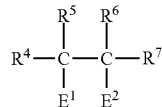

(II)

where $R^4$, $R^5$, $R^6$, and $R^7$ are independently chosen from hydrogen, a C1-C20 alkyl, and a C6-C10 aryl, and $E^1$ and $E^2$ may be as previously described. In embodiments, $R^4$-$R^7$ are independently chosen from a C1-20 alkyl including, but not limited to, methyl, ethyl, propyl, isopropyl, butyl, isobutyl, tert-butyl, pentyl, hexyl, etc.

In embodiments, the dianionic chelating ligand $E^1$-$X^1$-$E^2$ is represented by the formula:

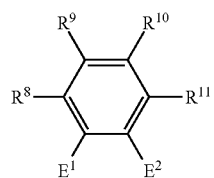

(III)

where $R^8$, $R^9$, $R^{10}$, and $R^{11}$ are independently chosen from hydrogen and a C1-C20 alkyl, and $E^1$ and $E^2$ may be as previously described. In embodiments, $R^8$-$R^{11}$ are independently chosen from hydrogen and a C1-C10 alkyl, even a C1-C6 alkyl. Examples of suitable alkyl groups for $R^8$-$R^{11}$ include but are not limited to, methyl, ethyl, propyl, isopropyl, butyl, isobutyl, tert-butyl, pentyl, hexyl, etc. In one embodiment, $R^8$ and $R^{10}$ are a C1-C10 alkyl, and $R^9$ and $R^{11}$ are each hydrogen. In one embodiment, $R^8$ and $R^{10}$ are each tert-butyl.

The $E^1$ and $E^2$ groups may be the same or different from one another in the dianionic chelating ligand. In embodiments, the $E^1$ and $E^2$ groups are each O. In other embodiments, $E^1$ is O, and $E^2$ is S.

The chelating diene compounds for $R^1$—$X^2$—$R^2$ are not particularly limited and can be chosen from a variety of diene compounds. Examples of suitable chelating dienes include, but are not limited to, 1,3-butadiene, isoprene, 2,3-dimethylbutadiene, 1,4-diphenyl-1,3-butadiene, 1,4-cyclohexadiene, 1,4-hexadiene, 2,4-hexadiene, 1,5-hexadiene, 1,5-cyclooctadiene, 1,5-dimethyl-1,5-cyclooctadiene, 1,6-dimethyl-1,5-cyclooctadiene, 1,3 dodecadiene, norbornadiene, dicyclopentadiene, etc.

In one embodiment, the unsaturated compound is chosen from an alkenyl silicone. The alkenyl silicone may be an alkenyl functional silane or siloxane that is reactive to hydrosilylation. The alkenyl silicone may be cyclic, aromatic, or a terminally-unsaturated alkenyl silane or siloxane. The alkyenyl silicone may be chosen as desired for a particular purpose or intended application. In one embodiment the alkenyl silicone comprises at least two unsaturated groups and has a viscosity of at least about 50 cps at 25° C. In one embodiment the alkenyl silicone has a viscosity of at least about 75 cps at 25° C.; at least about 100 cps at 25° C.; at least 200 cps at 25° C.; even at least about 500 cps at 25° C. Here as elsewhere in the specification and claims, numerical values may be combined to form new and non-disclosed ranges.

In one embodiment, the alkenyl silicone is a compound of the formula:

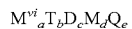

$$M^{vi}_a T_b D_c M_d Q_e$$

wherein $M^{vi}_a = R^{12}_2 R^{13} SiO_{1/2}$; $T_b = R^{14} SiO_{3/2}$ where $R^{14}$ is chosen from $R^{12}$ or $R^{13}$; $D_c = R^{12} R^{14} SiO_{2/2}$ where $R^{14}$ is chosen from $R^{12}$ or $R^{13}$; $M_d = R^{12}_3 SiO_{1/2}$; and $Q_e = SiO_{4/2}$; $R^{12}$ is independently selected from a monovalent hydrocarbon radical having one to forty carbon, optionally containing at least one heteroatom; and $R^{13}$ is selected from a terminal olefinic monovalent hydrocarbon radical having two to forty carbon atoms, optionally containing at least one heteroatom. The composition of the alkenyl silicone is such as to provide at least two unsaturated groups reactive to hydrosilylation per chain; a≥0, b≥0, d≥0, e≥0; values for c in particular are determined by the desired properties and attributes of the cross-linked material so that the sum a+b+c+d+e is in the range 50-20,000. In embodiments, the alkenyl silicone is a compound of the formula $M^{vi} D_c M^{vi}$.

Particular alkenyl silicones and cross-linkers chosen to generate desired mechanical, thermal and other properties of the product can be determined by those skilled in the art. Terminally-unsaturated alkenyl silicone materials are particularly suitable for forming cured or crosslinked products such as coatings and elastomers. It is also understood that two or more of these alkenyl silicones, independently selected, may be used in admixture in a cure formulation to provide desired properties.

The silyl hydride employed in the reactions is not particularly limited. It can be, for example, any compound chosen from hydrosiloxanes including those compounds of the formula $M_{a'} M^H_{b'} D_{c'} D^H_{d'} T_{e'} T^H_{f'} Q_{g'}$, where M, D, T, and Q have their usual meaning in siloxane nomenclature. The subscripts a', b', c', d', e', f, and g are such that the molar mass of the siloxane-type reactant is between 100 and 100,000 Dalton. In one embodiment, an "M" group represents a monofunctional group of formula $R^{15}_3 SiO_{1/2}$, a "D" group represents a difunctional group of formula $R^{15}_2 SiO_{2/2}$, a "T" group represents a trifunctional group of formula $R^{15} SiO_{3/2}$, and a "Q" group represents a tetrafunctional group of formula $SiO_{4/2}$, an "$M^H$" group represents $HR^{15}_2 SiO_{1/2}$, a "$T^H$" represents $HSiO_{3/2}$, and a "$D^H$" group represents $R^{15} HSiO_{2/2}$. Each occurrence of $R^{15}$ is independently C1-C40 alkyl, C1-C40 substituted alkyl, C6-C14 aryl or substituted aryl, wherein $R^{15}$ optionally contains at least one heteroatom. In one embodiment, the substantially linear hydrogen siloxane is chosen from $MD_cD^H_dM$, $MD^H_dM$, or mixtures thereof. In embodiments, $R^{15}$ is chosen from a C1-C20 alkyl, a C1-C10 alkyl, or a C1-C6 alkyl. In embodiments, $R^{15}$ is methyl.

The components (a) and (b) that are used in the compositions of this invention are not narrowly limited. Said amounts, expressed in terms of the ratio of the number of silicon-bonded hydrogen atom of component (b) to the number of silicon-bonded olefinic hydrocarbon radicals of component (a), typically are sufficient to provide a value of said ratio from 1/100 to 110/1, from 1/20 to 20/1, and even from 0.5 to 20/1. Here as elsewhere in the specification and claims, numerical values can be combined to form new and alternative ranges.

Inhibitors for component (c) of the platinum group metal catalysts are well known in the organosilicon art. Examples of suitable inhibitors include, but are not limited to, ethylenically unsaturated amides, aromatically unsaturated amides, acetylenic compounds, ethylenically unsaturated isocyanates, olefinic siloxanes, unsaturated hydrocarbon diesters, unsaturated hydrocarbon mono-esters of unsaturated acids, conjugated or isolated ene-ynes, hydroperoxides, ketones, sulfoxides, amine, phosphines, phosphites, nitrites, diaziridines, etc. Particularly suitable inhibitors for the compositions are alkynyl alcohols and maleates.

The amount of component (c) to be used in the compositions is not critical and can be any amount that will retard the above described platinum catalyzed hydrosilylation reaction at room temperature while not preventing said reaction at moderately elevated temperature, i.e. a temperature that is 25 to 125° C. above room temperature. No specific amount of inhibitor can be suggested to obtain a specified bath life at room temperature since the desired amount of any particular inhibitor to be used will depend upon the concentration and type of the platinum metal containing catalyst, the nature and amounts of components a and b. The range of component c can be 0 to about 10% weight, about 0.001 wt to 2% by weight, even about 0.12 to about 1 by weight. Here as elsewhere in the specification and claims, numerical values can be combined to form new and alternative ranges. In one embodiment, the compositions can be free of any inhibitor component (c).

The composition may optionally further comprise one or more additional ingredients, such as filler, filler treating agent, plasticizer, spacer, extender, biocide, stabilizer, flame retardant, surface modifier, pigment, anti-aging additive, rheological additive, corrosion inhibitor, surfactant or combination thereof.

The concentration of platinum catalyst used in the present process can be varied. In one embodiment, the concentration of platinum is from about 100 parts per billion (ppb) to about 100 part per million (ppm); from about 500 ppb to about 100 ppm; from about 1 ppm to about 50 ppm; even from about 5 ppm to about 30 ppm. Here as elsewhere in the specification and claims, numerical values can be combined to form new and alternative ranges.

The platinum catalyst may be dissolved in solvent to improve ease of handling. The solvent is not limited and can be either polar or non-polar. Any solvent can be used in the method of the invention, as long as it facilitates the dissolution of the platinum catalyst, without deleterious effects.

Accordingly, in some embodiments, the present invention is also directed to the compositions produced from the above described methods. These compositions contain the hydrosilylated products of the silylhydride and the compound having at least one unsaturated group. Products can be produced by reacting the components of the composition under conditions to promote formation of a crosslinked product. In one embodiment, the components can be provided as a one part composition comprising at least components (a), (b), and (d), and optionally (c). In another embodiment, the components can be provided in two or more separate compositions and mixed prior to curing. Curing may be accomplished by reacting the components at a temperature of from about 25 to 200° C., and in one embodiment from a temperature of from about 25 to about 125° C.

In still another embodiment, the process for producing a crosslinked product for release coatings comprises reacting (a) an alkenyl silicone, (b) a hydrogen siloxane, (c) a cure inhibitor, and (d) a catalyst, optionally in the presence of a solvent, wherein the catalyst comprises a compound of the formula:

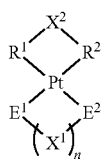

Formula (I)

wherein $R^1$—$X^2$—$R^2$ is a diene that is bonded to platinum in an $\eta^4$-mode and is a branched chain, an unbranched chain, a cyclic system, or a bicyclic system having 4 to 30 carbon atoms; $E^1$-$X^1$-$E^2$ is an alpha- or beta-hydroxy acid ligand; $X^2$ is a divalent hydrocarbyl such as substituted or unsubstituted alkylene, arylene, or cycloalkylene group, whereby the bonding olefin moieties are terminal and/or internal and $X^2$ represents bridges between the olefinic groups; and n is 0, 1, 2, 3, or 4.

Specific examples of suitable dianionic chelating ligands from hydroxyacids include, but are not limited to O,O-dianion of, lactic acid, 2-hydroxyhexanoic acid, isobutryric acid, 3-hydroxypropanoic acid, salicylic acid, etc.

The hydrosilylated products that are produced by the process of the present invention have uses in the synthesis of silicone materials such as elastomers, coatings, e.g., release liner coatings, for molding etc. When provided as a coating, the composition is coated onto at least a portion of a surface of a substrate. The amount of the surface coated with the coating composition can be selected as desired for a particular purpose or intended application. Release coatings are part of a laminate wherein a release coating is coated upon a substrate. Generally substrates suitable for release coatings include, but are not limited to, paper, polymeric films such as those consisting of polyethylene, polypropylene, polyester, etc. The use of the present catalysts in coating compositions has been found to provide particularly good curing in a short period of time including in about 10 seconds or less; about 7 seconds or less, even about 5 seconds or less. In one embodiment, curing can be effected in about 2 to about 10 seconds, even about 2 to about 5 seconds. Further, the cured compositions exhibit good binding and can be anchored to substrates including, for example, to paper.

The following examples are intended to illustrate, but in no way limit the scope of the present invention. All parts and percentages are by weight and all temperatures are in Celsius unless explicitly stated otherwise. All patents, other publications, and U.S. patent applications referred to in the instant application are incorporated herein by reference in their entireties.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

EXAMPLES

Aspects of this disclosure will now be described and may be further understood with respect to the following examples. The examples are intended to be illustrative only and are to be understood as not limiting the invention disclosed herein in any way as to materials, or process parameters, equipment or conditions.

Experimental

Reactions and manipulations were performed under nitrogen, using standard Schlenk-line techniques for the preparation of the platinum complexes. Crosslinking reactions were performed in air. The preparation of the platinum complexes was performed according to published procedures for $^tBu_2$-$C_6H_2O_2$PtCOD (Boyer et al. Inorg. Chem 2009, 48, 638-645) and $C_6H_4S_2$PtCOD (Rath et al, Inorg. Chim. Acta, 2007, 306(5), 1767-1770.) The $^1H$, $^{13}C$ and $^{29}Si$ NMR spectra were recorded on a Bruker 200 mHZ and 400 mHz spectrometers. Unless otherwise stated formulations used in examples contain SilForce™ SL6900 ($M^{vi}D_{80}M^{vi}$), and Silforce™ SL6020D1 ($MD_{15}D^H_{30}M$) at Si—H/Si-vinyl ratio of 1.8. The SL6900, SL6020D1, SL4400 ($MD_{25}D^H_{27}M$), SS4300C ($MD^H_{45}M$) and SL4500 ($MD^H_{25}M$) were obtained from Momentive Performance Materials. The following abbreviations and terms are used: THF, tetrahydrofuran; NMR, Nuclear Magnetic Resonance; nbd, norbornadiene; dcp, dicyclopentadiene, S61, 3,5-dimethylhex-1-yn-3-ol, ECH, 1-ethynyl-1-cyclohexanol.

3,5-$^tBu_2$-catecholatePtCOD:

A flask was charged with 3,5-ditertbutylcatechol (0.21 g, 1 mmol) and potassium tertbutoxide (0.22 g, 2 mmol) were added to a schlenk flask. The flask was purged with $N_2$. The material was dissolved in 30 mL of dry THF. A second flask was charged with PtCODCl$_2$ (0.35 g, 1 mmol). The flask was purged with $N_2$. The PtCODCl$_2$ was dissolved in 60 mL of $CH_2Cl_2$. The deprotonated catechol was added to the PtCODCl$_2$ solution via cannula. Immediately a dark orange solution formed and a white precipitate. The material was stirred for 3 hours. The material was filtered to remove the white solid. The orange filtrate was concentrated under vacuum. The product was extracted in DCM/hexanes (60 mL, 2:1). Obtained 0.44 g orange solid (90% yield). Obtained 0.44 g orange solid (90% yield). $^1H$ NMR (CDCl$_3$): 6.78 (s, 1H, aryl), 6.64 (s, 1H, aryl), 5.31 (m, $J_{Pt-H}$=77 Hz, 4H, CH), 2.64 (bs, 4H, CH$_2$), 2.30 (bs, 4H, CH$_2$), 1.38 (s, 9H, $^tBu$), 1.27 (s, 9H, $^tBu$). $^{13}C$ NMR (CDCl$_3$): 160.9 (C=O), 157.6 (C=O), 140.5 ($C_{aryl}$), 135.0

($J_{C-Pt}$=53.7 Hz, $C_{aryl}$), 112.5 ($CH_{aryl}$), 110.5 ($J_{Pt-C}$=61.6 Hz, $CH_{aryl}$), 87.1 ($J_{Pt-C}$=173.8 Hz, C≡C), 32.1 ($C^tBu$), 30.0 ($^tBu$), 29.8 ($^tBu$), 29.7 ($CH_2$). $^{195}$Pt NMR ($CDCl_3$): −3210.

PinacolatePtCOD:

A dry round bottomed flask was charged with 2,3-dimethyl-2,3-butanediol (1.2 g, 10.2 mmol), under nitrogen, and anhydrous THF (30 mL) was added. A separate schlenk flask was charged with potassium tert-butoxide (2.2 g, 20 mmol) under a nitrogen atmosphere and dissolved in anhydrous THF (30 mL). A separate round bottom was charged with a solution of $PtCODCl_2$ (3.6 g, 9.7 mmol) in dichloromethane (150 mL), and placed under nitrogen atmosphere. The 2,3-dimethyl-2,3-butanediol solution was transferred via cannula to the potassium tert-butoxide solution. The cloudy mixture was allowed to stir for 5 min before being transferred via cannula to the $PtCODCl_2$ solution. This yielded a yellow solution that slowly darkened as it stirred under nitrogen at room temperature. After 4 hours the slightly cloudy solution was stopped stirring and filtered through filter paper. The filtrate was reduced under vacuum to a brown solid. The isolated brown solid was dissolved in 25 mL of dichloromethane and diluted with 250 mL of heptanes. A brown ppt formed and was filtered off, the filtrate was reduced to obtain 3.2 g of a tan solid (79% yield). $^1$H NMR ($CDCl_3$): 4.83 (bs, $J_{Pt-H}$=61.6 Hz, 4H, CH), 2.53 (m, 4H, $CH_2$), 2.15 (m, 4H, $CH_2$), 1.21 (s, 12H, $CH_3$). $^{13}$C NMR ($CDCl_3$): 88.2 ($J_{Pt-C}$=164.5 Hz, C=C), 86.4 (CO), 30.0 ($CH_2$), 27.2 ($J_{Pt-C}$=20.5, $CH_3$). $^{195}$Pt NMR ($CDCl_3$): −3180.

$C_6H_4$ONMePtCOD:

This material was prepared similar to 3,5-$^tBu_2$-catecholatePtCOD except the material was extracted into diethyl ether. The solvent was removed under vacuum to afford an orange solid. Yield 81%. $^1$H NMR ($CDCl_3$): 6.5-6.9 ppm (m, 4H, aryl), 5.22 (bs, $J_{Pt-H}$=54 Hz, 2H, CH), 4.03 (bs, $J_{Pt-H}$=65 Hz, 2H, CH), 3.19 (s, $J_{Pt-H}$=30 Hz, 3H, N-Me), 2.2-2.8 (m, 8H, $CH_2$). $^{13}$C NMR ($CDCl_3$): 161.4 (C=O), 151.8 ($J_{Pt-C}$=44.8 Hz, C=N), 118.2 ($CH_{aryl}$), 116.6 ($CH_{aryl}$), 113.4 ($J_{Pt-C}$=59.6 Hz, $CH_{aryl}$), 108.7 ($J_{Pt-C}$=39 Hz, $CH_{aryl}$), 88.9 ($J_{Pt-C}$=148.1, C≡C), 84.3 ($J_{Pt-C}$=188.6, C≡C), 36.7 ($J_{Pt-C}$=56.9 Hz, N-Me), 31.1 ($CH_2$), 29.2 ($CH_2$). $^{195}$Pt NMR ($CDCl_3$): −3498 ppm.

$C_6H_4(NMe)_2$PtCOD:

This material was prepared similar to 3,5-$^tBu_2$-catecholatePtCOD except the material was extracted into diethyl ether. The solvent was removed under vacuum. The brown tacky residue was recrystallized from DCM/pentane. Obtained 38% yield of a dark brown microcrystalline material. $^1$H NMR ($CDCl_3$): 6.67-6.86 (m, 4H, aryl), 4.79 (bs, 4H, $J_{Pt-H}$=54.7 Hz, CH), 3.32 (bs, 6H, $J_{Pt-H}$=29.7 Hz, N-Me), 2.33-2.76 (m, 8H, $CH_2$). $^{13}$C NMR ($CDCl_3$): 150.0 ($J_{Pt-C}$=40.7 Hz, C=N), 116.1 ($CH_{aryl}$), 106.8 ($J_{Pt-C}$=40.5 Hz, $CH_{aryl}$), 83.1 ($J_{Pt-C}$=162 Hz, C≡C), 36.9 ($J_{Pt-C}$=46.4 Hz, N-Me), 30.4 ($CH_2$). $^{195}$Pt NMR ($CDCl_3$): −3828 ppm.

$C_6H_4S_2$PtCOD:

This material was prepared in a similar manner to 3,5-$^tBu_2$-catecholatePtCOD with the following exceptions. Sodium hydride (159 mg, 2 equiv, 60% emulsion in mineral oil) was employed instead of potassium tert-butoxide. The crude solid was purified by crystallization from dichlormethane/heptane mixture to afford a yellow solid. Yield 28%. $^1$H NMR ($CDCl_3$): 7.55 (dd, J=6.4 Hz, J=2.8 Hz, 2H, aryl), 6.92 (dd, J=6.2 Hz, J=3.1 Hz, 2H, aryl), 5.50 (bs, $J_{Pt-H}$=53.1 Hz, 4H, CH), 2.56 (m, 8H, $CH_2$). $^{13}$C NMR ($CDCl_3$): 145.8 (C=S), 127.9 ($J_{Pt-C}$=79.2 Hz, $CH_{aryl}$), 123.0 ($CH_{aryl}$), 92.5 ($J_{Pt-C}$=117.4 Hz, C≡C), 30.5 ($CH_2$). $^{195}$Pt NMR ($CDCl_3$): −4068.

$C_6H_4$SOPtCOD:

This material was prepared in a similar manner to 3,5-$^tBu_2$-catecholatePtCOD. Orange solid. Yield 73%. $^1$H NMR ($CDCl_3$): 7.37 (d, J=7.5 Hz, 1H, aryl), 6.87 (m, 2H, aryl), 6.67 (m, 1H, aryl), 5.69 (bs, $J_{Pt-H}$=54.1 Hz, 2H, CH), 5.69 (bs, $J_{Pt-H}$=61.6 Hz, 2H, CH), 2.63 (m, 4H, $CH_2$), 2.39 (m, 4H, $CH_2$). $^{13}$C NMR ($CDCl_3$): 171.1 (C=S), 130.8 (C=O), 127.9 ($J_{Pt-C}$=54.25 Hz, $CH_{aryl}$), 124.2 ($CH_{aryl}$), 118.5 ($CH_{aryl}$), 116.1 ($J_{Pt-C}$=78.92 Hz, $CH_{aryl}$), 100.6 ($J_{Pt-C}$=113.4 1-Hz, C≡C), 79.8 ($J_{C-Pt}$=174.61 Hz, C≡C), 31.3 ($CH_2$), 28.9 ($CH_2$). $^{195}$Pt NMR ($CDCl_3$): −3583.

SalicylatePtCOD):

This material was prepared in a similar manner to 3,5-$^tBu_2$ catecholatePtCOD with the following exceptions. The $PtCODCl_2$ solution was added to the stirring solution of salicylic acid and KO$^t$Bu in THF. The isolated material was washed with toluene isolating a yellow solid. Yield 49%. $^1$H NMR ($CDCl_3$): 8.12 (dd, J=8.3 Hz, J=1.6 Hz, 1H, aryl), 7.25 (td, J=7.5 Hz, J=1.5 Hz, 1H, aryl), 6.80 (t, J=7.5 Hz, 1H, aryl), 6.72 (d, J=8.3 Hz, 1H, aryl), 5.36 (bs, $J_{Pt-H}$=66.0 Hz, 4H, CH), 2.76 (m, 4H, $CH_2$), 2.32 (m, 4H, $CH_2$). $^{13}$C NMR ($CDCl_3$): 165.7 (OCO), 164.7 ($C_{Ph}$) 133.1 ($C_{Ph}$), 132.7 ($C_{Ph}$), 119.5 ($J_{Pt-C}$=50.8 Hz, $C_{Ph}$), 118.1 ($C_{Ph}$), 117.6 ($C_{Ph}$O), 95 ($J_{Pt-C}$=168.9 Hz, C≡C), 94.9 ($J_{Pt-C}$=184.9 Hz, C≡C), 29.8 ($CH_2$), 29.7 ($CH_2$). $^{195}$Pt NMR ($CDCl_3$): −2899.

IsobutyratePtCOD:

This material was prepared in a similar manner to 3,5-$^tBu_2$ catecholatePtCOD with the following exceptions. The final material was precipitated from a DCM/heptane mixture isolating a brown solid. Yield 61%, $^1$H NMR ($CDCl_3$): 5.17 (bs, $J_{Pt-H}$=66.2 Hz, 4H, CH), 2.68 (m, 4H, $CH_2$), 2.28 (m, 4H, $CH_2$) 1.39 (s, 6H, $CH_3$). $^{13}$C NMR ($CDCl_3$): 193.5 (OCO), 93.0 ($J_{Pt-C}$=181.5 Hz, C≡C), 89.9 ($J_{Pt-C}$=157.9 Hz, C≡C), 79.6 (CO), 30.7 ($CH_3$), 29.9 ($CH_2$). $^{195}$Pt NMR ($CDCl_3$): −3092.

LactatePtCOD:

This material was prepared in a similar manner to 3,5-$^tBu_2$-catecholatePtCOD with the following exceptions. The $PtCODCl_2$ solution was added to the stirring solution of lactic acid and KOtBu in THF (due to the latter's insolubility). The crude mixture was dissolved in DCM and diluted with heptanes to isolate a brown solid that contained solvent materials. The material decomposed upon standing. $^1$H NMR ($CDCl_3$): 5.22 (s, $J_{Pt-H}$=71.1 Hz, 2H, CH), 5.15 (s, $J_{Pt-H}$=62.9 Hz, 2H, CH), 4.59 (q, J=6.87 Hz, 1H, OCH), 2.69 (m, 4H, $CH_2$), 2.27 (m, 4H, $CH_2$), 3.43 (d, J=6.87 Hz, 3H, $CH_3$). $^{13}$C NMR ($CDCl_3$): 192.3 (OCO), 93.5 ($J_{Pt-C}$=183.7 Hz, C≡C), 93.3 ($J_{Pt-C}$=184.0 Hz, C≡C), 89.9 ($J_{Pt-C}$=160.6 Hz, C≡C), 89.8 ($J_{Pt-C}$=161.4 Hz, C≡C), 75.6 (OCH), 29.9 ($CH_2$), 29.8 ($CH_2$), 29.7 ($CH_2$), 29.6 ($CH_2$). $^{195}$Pt NMR ($CDCl_3$): −3079.

PropanediolatePtCOD:

This material was prepared in a similar manner to 3,5-$^tBu_2$ catecholatePtCOD with the following exceptions. The crude mixture was filtered, and the filtrate was reduced to a dark semi-solid. The semi-solid was analyzed by $^1$H NMR to show impurities of solvent materials and excess propanediol. The material decomposed upon standing. $^1$H NMR ($CDCl_3$): 4.79 (s, $J_{Pt-H}$=61.7 Hz, 4H, CH), 3.85 (t, J=4.93 Hz, 4H, 4H, OCH), 2.66 (m, 4H, $CH_2$), 2.14 (m, 4H, $CH_2$), 1.80 (quint, J=5.60 Hz, 2H, $CH_2$).

3,5-$^tBu_2$-$C_6H_2O_2$Ptnbd:

The $PtnbdCl_2$ (0.35 g, 0.09 mmol) and catechol (0.2 g, 0.09 mmol) were dissolved in 40 mL of DCM. The material was purged with $N_2$ for 15 minutes. The $NEt_3$ (1 mL, 7.2 mmol) was added to the colorless solution. Immediately an orange solution formed. The material was stirred for several hours. The solvent was removed under vacuum. The orange solid was washed with DI water (3×100 mL). The orange solid was extracted into DCM and filtered. The orange liquid was concentrated under vacuum. Obtained 0.387 g of orange solid (85% yield). $^1$H NMR (CDCl$_3$): 6.77 (d, 1H, aryl), 6.63 (d, 1H, aryl), 4.92 (bs, $J_{Pt-H}$=69 Hz, 4H, CH), 4.26 (bs, 2H, CH), 1.51 (s, 2H, CH$_2$), 1.37 (s, 9H, $^t$Bu), 1.26 (s, 9H, $^t$Bu). $^{13}$C NMR (CDCl$_3$): 161.2 (C=O), 158.1 (C=O), 140.5 (C$_{aryl}$), 134.6 (J$_{Pt-C}$=54.2 Hz, C$_{aryl}$), 112.5 (CH$_{aryl}$), 110.0 (J$_{Pt-C}$=68.9, C$_H$aryl), 67.5 (J$_{Pt-C}$=125.2 Hz, CH$_2$), 65.7 (J$_{Pt-C}$=117.5 Hz, C=C), 65.5 (J$_{Pt-C}$=123 Hz, C=C), 46.9 (J$_{Pt-C}$=48.4 Hz, CH), 34.8 (C$^t$Bu), 34 (C$^t$Bu), 32 ($^t$Bu), 29.5 ($^t$Bu). $^{195}$Pt NMR (CDCl$_3$): −3199 ppm.

3,5-$^t$Bu$_2$-C$_6$H$_2$O$_2$PtC$_6$H$_{10}$:

This material was prepared from PtC$_6$H$_{10}$Cl$_2$ in a manner similar to the 3,5-$^t$Bu$_2$-C$_6$H$_2$O$_2$Ptnbd synthesis except the material was crystallized from DCM/heptane. Obtained an orange solid (55% yield). $^1$H NMR (CDCl$_3$): 6.78 (d, J=2.0 Hz, 1H, aryl), 6.66 (d, J=2.0 Hz, 1H, aryl), 5.29 (m, 2H, CH), 4.67 (dd, J=8.0 Hz, J=5.3 Hz, J$_{Pt-H}$=63.6 Hz, 2H, CH$_2$), 3.50 (d, J=13.7 Hz, J$_{Pt-H}$=52.2, 2H, CH$_2$), 2.66 (m, 2H, CH$_2$), 2.25 (m, 2H, CH$_2$), 1.38 (s, 9H, $^t$Bu), 1.27 (s, 9H, $^t$Bu). $^{13}$C NMR (CDCl$_3$): 161.3 (C=O), 157.7 (C=O), 140.9 (C$_{aryl}$), 135.0 (C$_{aryl}$), 112.8 (CH$_{aryl}$), 110.5 (J$_{Pt-C}$=63.4 Hz, CH$_{aryl}$), 92.40 (J$_{Pt-C}$=150.8 Hz, C=C), 92.3 (J$_{Pt-C}$=150.8 Hz, C=C), 65.1 (J$_{Pt-C}$=170.2 Hz, CH$_2$), 64.8 (J$_{Pt-C}$=176.2 Hz, CH$_2$), 32.1 (CH$_2$), 31.39 (C$^t$Bu), 31.4 (C$^t$Bu), 29.7 ($^t$Bu). $^{195}$Pt NMR (CDCl$_3$): −3320.

3,5-$^t$Bu$_2$-C$_6$H$_2$O$_2$Ptdcp:

This material was prepared from PtdcpCl2 in a manner similar to the 3,5-$^t$Bu$_2$-C$_6$H$_2$O$_2$Ptnbd synthesis above except the material was recrystallized from DCM/pentane. Obtained an orange solid (68% yield). $^1$H NMR (CDCl$_3$): 6.73 (d, 1H, aryl), 6.62 (d, 1H, aryl), 6.45 (bs, 1H, CH), 6.07 (bs, 1H, CH), 5.70 (bs, 1H, CH), 5.25 (bs, 1H, CH), 3.81 (m, 1H, CH), 3.50 (bs, 1H, CH), 2.83 (m, 2H, CH), 1.9-2.40 (m, 4H, CH$_2$), 1.38 (s, 9H, $^t$Bu), 1.26 (s, 9H, $^t$Bu). $^{13}$C NMR (CDCl$_3$): 160.0 (C=O), 157.6 (C=O), 140.8 (C$_{aryl}$), 134.9 (C$_{aryl}$), 112.4 (CH$_{aryl}$), 110.7 (J$_{Pt-C}$=63.3 Hz, CH$_{aryl}$), 100 (J$_{Pt-C}$=164.6 Hz, C=C), 90.4 (J$_{Pt-C}$=149 Hz, C=C), 89.0 (J$_{Pt-C}$=149 Hz, C=C), 83.3 (J$_{Pt-C}$=187.2 Hz, C=C), 60.8 (J$_{Pt-C}$=72.2 Hz, CH), 55.2 (CH$_2$), 44.6 (CH), 42.8 (CH), 34.8 (C$^t$Bu), 33.2 (C$^t$Bu), 32.0 ($^t$Bu), 29.7 ($^t$Bu). $^{195}$Pt NMR (CDCl$_3$): −3093 ppm.

General Procedure for DSC

A master batch of formulation was prepared for each 3,5-dimethyl-1-hexyn-3-ol wt % loading. For the 0.23 wt % mater batch, the SL6900 (168.57 g), SL6020D1 (10.07 g) and 3, 5 dimethyl 1-hexyn-3-ol (0.42 g) were added to an olive jar. The formulation was mixed by vigorously shaking. All formulations were prepared similarly except for 0.009 wt % 3, 5 dimethyl 1-hexyn-3-ol formulation. For the formulation with 0.009 wt % 3, 5 dimethyl 1-hexyn-3-ol, a 10% solution of 3, 5 dimethyl 1-hexyn-3-ol in toluene was employed instead of neat 3, 5 dimethyl 1-hexyn-3-ol. The catalyst solution was prepared by dissolving the catalyst (0.023 mmol) in solvent (2 mL). An aliquot of the master batch (10 g) was added to a vial. The catalyst solution (140 uL) was added immediately before the DSC was run. The formulation was mixed by vigorously shaking it. The DSC was run. The DSC program equilibrates at 25° C. and then ramps 10° C./min to 200° C.

General Procedure for Bath Life

A master batch of formulation was prepared. An aliquot of the master batch formulation (150 g) was added to an olive jar. The catalyst solutions were prepared (0.0045 g Pt in 1 mL of CH$_3$Cl). The catalyst solution were added to the olive jar. The formulations were placed in a 25° C. bath for 30 minutes. The initial viscosity was taken. The samples were placed in a 40° C. bath for 4 hr in an open container. The samples were placed in the 25° C. bath. The 4 hr viscosity was taken.

General Procedure for Pilot Coater Runs

A stock batch of formulation was prepared with SL6900 (700 g) and SL6020D1 (41.8 g) and inhibitor. The material was mixed. The catalyst solution was prepared by dissolving the Pt complex (0.1 mmol) in 5 mL of toluene. The catalyst solution was added to the stock formulation. The material was run on a pilot coater. The coatings were analyzed by % extractables, coat weight, along with smear and migration tests.

General Procedure for Simple Crosslinking Test

A mixing cup is charged with ~50 g of UVLSR2060. A stock solution of the catalysts were prepared (0.011 g (pinacolate)PtCOD in 3 mL xylenes, etc). An aliquot of the catalyst solution is added to the mixing cup to give a 10 ppm Pt loading (0.3 mL of the pinacolatePtCOD stock solution). The material was speedmixed for 30 sec twice. The mixed formulation (~2 g) was added to an aluminum weigh boat. The material was placed in an oven at 120° C.

TABLE 1

DSC data for the crosslinking reaction of SL6900 and SL6020D1 with various Pt catalysts at various wt % loadings of 3,5-dimethyl-1-hexyn-3-ol.

| Compounds | Inhibitor Loading (% wt) | Onset (° C.) | Peak (° C.) | DH (J/g) | T95C (° C.) | DT95 (° C.) |
|---|---|---|---|---|---|---|
| Karstedt | 0 | — | — | — | — | — |
| Karstedt | 0.009 | 38.09 | 55.43 | 22.72 | 59.16 | 21.07 |
| Karstedt | 0.12 | 77.56 | 84.25 | 28.49 | 101.04 | 23.48 |
| Karstedt | 0.23 | 90.33 | 97.32 | 30.86 | 101.00 | 10.67 |
| PtCODCl$_2$ | 0 | 55.96 | 75.63 | 16.17 | 82.42 | 26.46 |
| PtCODCl$_2$ | 0.009 | 68.59 | 78.13 | 29.02 | 82.84 | 14.25 |
| PtCODCl$_2$ | 0.12 | 85.17 | 91.74 | 30.17 | 95.33 | 10.16 |
| PtCODCl$_2$ | 0.23 | 90.44 | 96.78 | 31.21 | 100.40 | 9.96 |
| $^t$Bu$_2$—C$_6$H$_2$O$_2$PtCOD | 0 | 49.03 | 79.07 | 22.11 | 93.98 | 44.95 |
| $^t$Bu$_2$—C$_6$H$_2$O$_2$PtCOD | 0.009 | 86.47 | 95.37 | 30.76 | 118.66 | 32.19 |
| $^t$Bu$_2$—C$_6$H$_2$O$_2$PtCOD | 0.12 | 98.97 | 109.43 | 28.32 | 126.94 | 27.97 |
| $^t$Bu$_2$—C$_6$H$_2$O$_2$PtCOD | 0.23 | 97.96 | 108.46 | 29.83 | 122.25 | 24.29 |
| C$_6$H$_4$ONMePtCOD | 0 | 63.71 | 68.98 | 11.52 | 80.98 | 17.27 |
| C$_6$H$_4$ONMePtCOD | 0.009 | 71.57 | 90.07 | 30.87 | 103.59 | 32.02 |
| C$_6$H$_4$ONMePtCOD | 0.12 | 90.41 | 104.63 | 29.87 | 114.4 | 23.99 |
| C$_6$H$_4$ONMePtCOD | 0.23 | 93.69 | 106.96 | 30.98 | 115.39 | 21.7 |

TABLE 1-continued

DSC data for the crosslinking reaction of SL6900 and SL6020D1 with various Pt catalysts at various wt % loadings of 3,5-dimethyl-1-hexyn-3-ol.

| Compounds | Inhibitor Loading (% wt) | Onset (° C.) | Peak (° C.) | DH (J/g) | T95C (° C.) | DT95 (° C.) |
|---|---|---|---|---|---|---|
| $C_6H_4S_2$PtCOD | 0 | 170.76 | 175.33 | 26.08 | 187.69 | 16.93 |
| $C_6H_4S_2$PtCOD | 0.009 | 170.22 | 173.89 | 28.47 | 186.95 | 16.73 |
| $C_6H_4S_2$PtCOD | 0.12 | 168.61 | 172.58 | 35.6 | 189.94 | 21.33 |
| $C_6H_4S_2$PtCOD | 0.23 | 170.27 | 174.18 | 27.59 | 186.21 | 15.94 |
| pinacolatePtCOD | 0 | — | — | — | — | — |
| pinacolatePtCOD | 0.009 | 55.56 | 66.86 | 22.85 | 69.74 | 14.18 |
| pinacolatePtCOD | 0.12 | 84.17 | 90.05 | 90.05 | 93.95 | 9.78 |
| pinacolatePtCOD | 0.23 | 87.44 | 94.15 | 30.41 | 98.6 | 11.16 |
| $C_6H_4(NMe)_2$PtCOD | 0 | 65.89 | 108.03 | 27.24 | 118.84 | 52.95 |
| $C_6H_4(NMe)_2$PtCOD | 0.009 | 87.83 | 121.06 | 29.12 | 138.26 | 50.43 |
| $C_6H_4(NMe)_2$PtCOD | 0.12 | 111.66 | 122.58 | 27.94 | 141.93 | 30.27 |
| $C_6H_4(NMe)_2$PtCOD | 0.24 | 105.24 | 115.63 | 28.59 | 136.06 | 30.82 |
| $C_6H_4$SOPtCOD | 0 | 83.77 | 94.91 | 30.73 | 113.69 | 29.92 |
| $C_6H_4$SOPtCOD | 0.009 | 95.51 | 102.91 | 29.47 | 120.86 | 25.35 |
| $C_6H_4$SOPtCOD | 0.12 | 91.47 | 97.72 | 28.94 | 103.13 | 11.66 |
| $C_6H_4$SOPtCOD | 0.24 | 97.07 | 103.07 | 30 | 106.65 | 9.58 |
| salicylatePtCOD | 0 | — | — | — | — | — |
| salicylatePtCOD | 0.009 | 60.99 | 70.26 | 21.29 | 74.58 | 13.59 |
| salicylatePtCOD | 0.12 | 83.45 | 89.57 | 31.1 | 93.83 | 10.38 |
| salicylatePtCOD | 0.24 | 88.72 | 95.36 | 32.13 | 100.08 | 11.36 |
| isobutyratePtCOD | 0 | — | — | — | — | — |
| isobutyratePtCOD | 0.009 | 61.63 | 70.71 | 27.3 | 74.86 | 13.23 |
| isobutyratePtCOD | 0.12 | 95.11 | 101.03 | 31.64 | 105.26 | 10.15 |
| isobutyratePtCOD | 0.24 | 92.76 | 99.17 | 33.19 | 104.8 | 12.04 |
| lactatePtCOD | 0 | — | — | — | — | — |
| lactatePtCOD | 0.009 | 67.5 | 75.46 | 29.77 | 80.18 | 33.97 |
| lactatePtCOD | 0.12 | 84.34 | 90.46 | 30.78 | 94.31 | 12.68 |
| lactatePtCOD | 0.24 | 89.65 | 96.23 | 31.39 | 100.42 | 10.58 |
| $^tBu_2$—$C_6H_2O_2$Ptnbd | 0 | 36.48 | 73.25 | 12.21 | 70.45 | 11.74 |
| $^tBu_2$—$C_6H_2O_2$Ptnbd | 0.009 | 64.06 | 72.75 | 29.36 | 76.74 | 25.94 |
| $^tBu_2$—$C_6H_2O_2$Ptnbd | 0.12 | 87.02 | 93.2 | 31.01 | 97.6 | 40.77 |
| $^tBu_2$—$C_6H_2O_2$Ptnbd | 0.24 | 92.15 | 99.24 | 31.22 | 103.89 | 25.94 |
| $^tBu_2$—$C_6H_2O_2$Ptdcp | 0 | 49.91 | 63 | 22.46 | 75.85 | 25.94 |
| $^tBu_2$—$C_6H_2O_2$Ptdcp | 0.009 | 88.98 | 97.26 | 31.62 | 129.75 | 40.77 |
| $^tBu_2$—$C_6H_2O_2$Ptdcp | 0.12 | 100.34 | 110.07 | 29.5 | 134.24 | 33.9 |
| $^tBu_2$—$C_6H_2O_2$Ptdcp | 0.24 | 103.49 | 113.99 | 28.89 | 135 | 31.51 |
| $^tBu_2$—$C_6H_2O_2$Pthexadiene | 0 | 36.73 | 60.06 | 18.34 | 70.59 | 33.86 |
| $^tBu_2$—$C_6H_2O_2$Pthexadiene | 0.009 | 76.77 | 86.23 | 31.25 | 116.94 | 40.17 |
| $^tBu_2$—$C_6H_2O_2$Pthexadiene | 0.12 | 93.995 | 102.74 | 31.07 | 123.75 | 29.755 |
| $^tBu_2$—$C_6H_2O_2$Pthexadiene | 0.24 | 99.11 | 108.32 | 30.65 | 125.74 | 26.63 |

All formulations contained a 30 ppm Pt loading.
$^tBu_2$—$C_6H_2O_2$ is 3,5-$^tBu_2$-catecholate Viscosity of formulations was evaluated with different catalysts at different loadings of diallyl maleate as inhibitor in a formulation containing SL6900 and SL6020 Formulations were heated to 40° C. All formulations contained a 30 ppm Pt loading. The results are shown in Table 2.

Working life of formulations with different catalysts was evaluated with no inhibitor in a formulation containing SL6900 and SL6020. Formulations were stored at 25° C. All formulations contained a 30 ppm Pt loading. Gel point is determined as when the material no longer flowed when container is inverted. The results are shown in Table 3.

TABLE 2

Viscosity data (bath life) for SL6900/SL6020 formulations containing Pt catalysts at a 30 ppm Pt loading with various diallyl maleate (DAM) loadings.

| Catalyst | Karstedt's | $^tBu_2C_6H_2O_2$PtCOD | Karstedt's | $^tBu_2C_6H_2O_2$PtCOD | Karstedt's | $^tBu_2C_6H_2O_2$PtCOD |
|---|---|---|---|---|---|---|
| St % DAM | 0.009 | 0.009 | 0.24 | 0.24 | 1 | 1 |
| Initial Visc. | NA | 120 | 112 | 104 | 104 | 104 |
| 4 hr Visc. | Gelled immediately | Gelled in 1.5 hr | 128 | 120 | 112 | 112 |
| 24 hr Visc. | | | 160 | 128 | 120 | 120 |
| 1 week Visc. | | | Gelled 2-3 days | 216 | 136 | 120 |
| 2 week Visc. | | | | | 184 | 160 |
| 3 week Visc. | | | | | 240 | 168 |
| 4 week Visc. | | | | | Gelled in 27 days | 232 |

TABLE 3

Working life of formulations containing Pt catalysts with no inhibitor.

| Catalyst | Time to gel |
|---|---|
| Karstedt's | 5 m |
| PinacolatePtCOD | 5 m |
| 3,5-$^tBu_2$-CatecholatePtCOD | 4.5 h |

Cure was evaluated for formulations coated on super calendered kraft paper using a variety of Pt catalysts. Curing of compositions on super calendered kraft (SCK) and glassine paper was evaluated. The formulation contained SL6900, SL6020 and 0.24 wt % S61]. All formulations contained a 30 ppm Pt loading. The material was coated and cured using a pilot coater. The line speed was 60 fpm and an oven dwell time of 10 sec. The results are shown in Table 4.

TABLE 4

Cure data for various Pt catalysts on SCK

| Compounds | Web Temperature (F.) | % Extractables |
|---|---|---|
| Karstedt | 278 | 1.6 |
| PtCODCl$_2$ | 272 | 18.9 |
| $^tBu_2$—C$_6$H$_2$O$_2$PtCOD | 297 | 4.6 |
| PinacolatePtCOD | 282 | 2.6 |
| C$_6$H$_4$ONMePtCOD | 285 | 7.3 |
| C$_6$H$_4$S$_2$PtCOD | 283 | 100 |
| C$_6$H$_4$(NMe)$_2$PtCOD | 283 | 23.8 |
| C$_6$H$_4$SOPtCOD | 285 | 96.2 |
| salicylatePtCOD | 272 | 2.3 |
| isobutyratePtCOD | 270 | 2.3 |
| hexadienePtCOD | 265 | 2.4 |
| nbdPtCOD | 264 | 2.6 |
| dcpPtCOD | 265 | 2.6 |

Cure was evaluated for formulations coated on SCK paper with diallyl maleate (DAM) as inhibitor using a variety of Pt catalysts. The formulations contained SL6900, SL6020, and 0.24 wt % DAM. All formulations contained a 30 ppm Pt loading. The material was coated and cured using a pilot coater. The line speed was 60 fpm and an oven dwell time of 10 sec. The results are shown in Table 5.

TABLE 5

Cure data for various Pt catalysts on SCK paper with DAM inhibitor.

| Compounds | Web Temperature (F.) | % Extractables |
|---|---|---|
| Karstedt | 294 | 1.7 |
| PtCODCl$_2$ | 292 | 5.5 |
| $^tBu_2$—C$_6$H$_2$O$_2$PtCOD | 300 | 5 |

Cure was evaluated using a simple cure test with LSR2060 formulation and a variety of Pt catalysts. All formulation contained 10 ppm Pt loading. The material was cured at 120° C.

TABLE 6

Cure data for various Pt catalysts in UVLSR 2060 formulations

| Catalyst | Cure time (minutes) |
|---|---|
| pinacolatePtCOD | 10 |
| $^tBu_2$-catecholatePtCOD | 10 |

Cure was evaluated for formulations coated on paper with using a variety of Pt catalysts. All formulations contained a 30 ppm Pt loading. The material was coated and cured using a pilot coater. The results are shown in Table 7-11.

TABLE 7

Pilot coater runs of formulations containing SL6900, SL6020D and varying amounts of ECH at a 30 ppm Pt loading) catalyst on SCK.

| Catalyst | ECH amount | Temperature (F.) | Oven Dwell Time (s) | Line Speed (fpm) | Extractables |
|---|---|---|---|---|---|
| PinacolatePtCOD | 0.07 | 300 | 4.5 | 200 | 2.7 |
| PinacolatePtCOD | 0.07 | 300 | 3 | 300 | 4.1 |
| PinacolatePtCOD | 0.07 | 300 | 1.5 s | 600 | 4.6 |
| PinacolatePtCOD | 0.07 | 325 | 4.5 | 200 | 1.8 |
| PinacolatePtCOD | 0.07 | 325 | 3 | 300 | 1.9 |
| PinacolatePtCOD | 0.07 | 325 | 1.5 | 600 | 2.8 |
| PinacolatePtCOD | 0.12 | 275 | 4.5 | 200 | 10.9 |
| PinacolatePtCOD | 0.12 | 275 | 3 | 300 | 14.6 |
| PinacolatePtCOD | 0.12 | 275 | 1.5 | 600 | 14.8 |
| PinacolatePtCOD | 0.12 | 300 | 4.5 | 200 | 3 |
| PinacolatePtCOD | 0.12 | 300 | 3 | 300 | 7.8 |
| PinacolatePtCOD | 0.12 | 300 | 1.5 | 600 | 8.1 |
| PinacolatePtCOD | 0.12 | 325 | 4.5 | 200 | 1.6 |
| PinacolatePtCOD | 0.12 | 325 | 3 | 300 | 1.8 |
| PinacolatePtCOD | 0.12 | 325 | 1.5 | 600 | 2.3 |
| PinacolatePtCOD | 0.25 | 275 | 4.5 | 200 | 41.4 |
| PinacolatePtCOD | 0.25 | 275 | 3 | 300 | 47.7 |
| PinacolatePtCOD | 0.25 | 275 | 1.5 | 600 | 48.6 |
| PinacolatePtCOD | 0.25 | 300 | 4.5 | 200 | 5.3 |
| PinacolatePtCOD | 0.25 | 300 | 3 | 300 | 10.1 |
| PinacolatePtCOD | 0.25 | 300 | 1.5 | 600 | 10 |
| PinacolatePtCOD | 0.25 | 325 | 4.5 | 200 | 2.2 |
| PinacolatePtCOD | 0.25 | 325 | 3 | 300 | 2.6 |
| PinacolatePtCOD | 0.25 | 325 | 1.5 | 600 | 4.1 |

TABLE 8

Pilot coater runs of formulations containing SL6900, SL6020, 0.25 wt % S61 and varying Si—H/Si-vinyl ratios at a 30 ppm Pt loading on SCK.

| Catalyst | Si—H/Si-Vi ratio | Temperature (F.) | Oven Dwell Time (s) | Line Speed (fpm) | Extractables |
|---|---|---|---|---|---|
| PinacolatePtCOD | 2.25 | 275 | 4.5 | 200 | 4 |
| PinacolatePtCOD | 2.25 | 275 | 3 | 300 | 3.6 |
| PinacolatePtCOD | 2.25 | 275 | 1.5 | 600 | 7.2 |
| PinacolatePtCOD | 2.25 | 325 | 4.5 | 200 | 1.8 |
| PinacolatePtCOD | 2.25 | 325 | 3 | 300 | 1.8 |
| PinacolatePtCOD | 2.25 | 325 | 1.5 | 600 | 2 |
| PinacolatePtCOD | 1.8 | 275 | 4.5 | 200 | 4.4 |
| PinacolatePtCOD | 1.8 | 275 | 3 | 300 | 13.2 |
| PinacolatePtCOD | 1.8 | 275 | 1.5 | 600 | 25.6 |
| PinacolatePtCOD | 1.8 | 325 | 4.5 | 200 | 2.2 |
| PinacolatePtCOD | 1.8 | 325 | 3 | 300 | 2.5 |
| PinacolatePtCOD | 1.8 | 325 | 1.5 | 600 | 2.2 |

TABLE 9

Pilot coater runs of formulations containing SL6900, 0.25 wt % S61 and various crosslinkers (Si—H/Si-vinyl 1.8) at a 30 ppm Pt loading on SCK.

| Catalyst | Hydride | Temperature | Oven Dwell Time | Line Speed (fpm) | % Extractables |
|---|---|---|---|---|---|
| pinacolatePtCOD | 88466 | 325 | 4.5 | 200 | 0.9 |
| pinacolatePtCOD | 88466 | 325 | 3 | 300 | 0.9 |
| pinacolatePtCOD | 88466 | 325 | 1.5 | 600 | 1.4 |
| 3,5-$^t$Bu$_2$-catecholatePtCOD | 88466 | 325 | 4.5 | 200 | 3.9 |
| 3,5-$^t$Bu$_2$-catecholatePtCOD | 88466 | 325 | 3 | 300 | 8.8 |
| 3,5-$^t$Bu$_2$-catecholatePtCOD | 88466 | 325 | 1.5 | 600 | 10.9 |
| PinacolatePtCOD | SS4300c | 325 | 4.5 | 200 | 20.7 |
| PinacolatePtCOD | SS4300c | 325 | 3 | 300 | 41.5 |
| PinacolatePtCOD | SS4300c | 325 | 1.5 | 600 | 28 |
| PinacolatePtCOD | SL4500 | 300 | 4.5 | 200 | 20.6 |
| PinacolatePtCOD | SL4500 | 300 | 3 | 300 | 44.4 |
| PinacolatePtCOD | SL4500 | 300 | 1.5 | 600 | 37.8 |
| PinacolatePtCOD | SL4500 | 325 | 4.5 | 200 | 5.6 |
| PinacolatePtCOD | SL4500 | 325 | 3 | 300 | 15 |
| PinacolatePtCOD | SL4500 | 325 | 1.5 | 600 | 19.6 |
| PinacolatePtCOD | SL6020 | 275 | 4.5 | 200 | 4.4 |
| PinacolatePtCOD | SL6020 | 275 | 3 | 300 | 13.2 |
| PinacolatePtCOD | SL6020 | 275 | 1.5 | 600 | 25.6 |
| PinacolatePtCOD | SL6020 | 300 | 4.5 | 200 | 2.2 |
| PinacolatePtCOD | SL6020 | 300 | 3 | 300 | 3.5 |
| PinacolatePtCOD | SL6020 | 300 | 1.5 | 600 | 9.4 |
| PinacolatePtCOD | SL6020 | 325 | 4.5 | 200 | 2.2 |
| PinacolatePtCOD | SL6020 | 325 | 3 | 300 | 2.5 |
| PinacolatePtCOD | SL6020 | 325 | 1.5 s | 600 | 2.2 |

TABLE 10

Pilot coater runs of formulations containing SL6900, SL6020D and various inhibitors (0.12 wt %) at a 30 ppm Pt loading on SCK.

| Catalyst | inhibitor | Temperature (F.) | Oven Dwell Time (s) | Line Speed (fpm) | Extractables |
|---|---|---|---|---|---|
| PinacolatePtCOD | S61 | 275 | 4.5 | 200 | 22.6 |
| PinacolatePtCOD | S61 | 275 | 3 | 300 | 20.9 |
| PinacolatePtCOD | S61 | 275 | 1.5 | 600 | 21.6 |
| PinacolatePtCOD | S61 | 300 | 4.5 | 200 | 3 |
| PinacolatePtCOD | S61 | 300 | 3 | 300 | 5.4 |
| PinacolatePtCOD | S61 | 300 | 1.5 | 600 | 5.2 |
| PinacolatePtCOD | S61 | 325 | 4.5 | 200 | 2.1 |
| PinacolatePtCOD | S61 | 325 | 3 | 300 | 1.8 |
| PinacolatePtCOD | S61 | 325 | 1.5 | 600 | 2.2 |
| PinacolatePtCOD | ECH | 275 | 4.5 | 200 | 10.9 |
| PinacolatePtCOD | ECH | 275 | 3 | 300 | 14.6 |
| PinacolatePtCOD | ECH | 275 | 1.5 | 600 | 14.8 |
| PinacolatePtCOD | ECH | 300 | 4.5 | 200 | 3 |
| PinacolatePtCOD | ECH | 300 | 3 | 300 | 7.8 |
| PinacolatePtCOD | ECH | 300 | 1.5 | 600 | 8.1 |
| PinacolatePtCOD | ECH | 325 | 4.5 | 200 | 1.6 |
| PinacolatePtCOD | ECH | 325 | 3 | 300 | 1.8 |
| PinacolatePtCOD | ECH | 325 | 1.5 | 600 | 2.3 |
| PinacolatePtCOD | DAM | 325 | 4.5 | 200 | 2.2 |
| PinacolatePtCOD | DAM | 325 | 3 | 300 | 1.8 |
| PinacolatePtCOD | DAM | 325 | 1.5 | 600 | 2.1 |

TABLE 11

Pilot coater runs of formulations containing SL6900, SL6020D and 0.25 wt % S61 at a 30 ppm Pt loading on various papers.

| Catalyst | paper | Temperature (F.) | Oven Dwell Time (s) | Extractables |
|---|---|---|---|---|
| pinacolatePtCOD | glassine | 250 | 4.5 | 14.9 |
| pinacolatePtCOD | glassine | 250 | 3 | 19.7 |
| pinacolatePtCOD | glassine | 250 | 1.5 | 34 |
| pinacolatePtCOD | glassine | 300 | 4.5 | 1.9 |
| pinacolatePtCOD | glassine | 300 | 3 | 2 |
| pinacolatePtCOD | glassine | 300 | 1.5 | 5.7 |
| pinacolatePtCOD | glassine | 350 | 4.5 | 1.2 |
| pinacolatePtCOD | glassine | 350 | 3 | 1.3 |
| pinacolatePtCOD | glassine | 350 | 1.5 s | 1.4 |
| pinacolatePtCOD | glassine | 275 | 4.5 | 1.2 |
| pinacolatePtCOD | glassine | 375 | 1.5 | 1.3 |
| pinacolatePtCOD | clay coat | 250 | 4.5 | 15.3 |
| pinacolatePtCOD | clay coat | 250 | 3 | 24.8 |
| pinacolatePtCOD | clay coat | 250 | 1.5 | 28.4 |
| pinacolatePtCOD | clay coat | 300 | 4.5 | 9 |
| pinacolatePtCOD | clay coat | 300 | 3 | 7.6 |
| pinacolatePtCOD | clay coat | 300 | 1.5 | 9.1 |
| pinacolatePtCOD | clay coat | 350 | 4.5 s | 2.6 |
| pinacolatePtCOD | clay coat | 350 | 3 | 2.7 |
| pinacolatePtCOD | clay coat | 350 | 1.5 | 2.7 |
| pinacolatePtCOD | clay coat | 375 | 4.5 | 2.2 |
| pinacolatePtCOD | clay coat | 375 | 3 | 2.3 |
| pinacolatePtCOD | clay coat | 375 | 1.5 | 2.4 |
| pinacolatePtCOD | SCK | 275 | 4.5 | 4.4 |
| pinacolatePtCOD | SCK | 275 | 3 | 13.2 |
| pinacolatePtCOD | SCK | 275 | 1.5 | 25.6 |
| pinacolatePtCOD | SCK | 300 | 4.5 | 2.2 |
| pinacolatePtCOD | SCK | 300 | 3 | 3.5 |
| pinacolatePtCOD | SCK | 300 | 1.5 | 9.4 |
| pinacolatePtCOD | SCK | 325 | 4.5 | 2.2 |
| pinacolatePtCOD | SCK | 325 | 3 | 2.5 |
| pinacolatePtCOD | SCK | 325 | 1.5 | 2.2 |

Embodiments of the invention have been described above and modifications and alterations may occur to others upon the reading and understanding of this specification. The claims as follows are intended to include all modifications and alterations insofar as they come within the scope of the claims or the equivalent thereof.

What is claimed is:

1. A process for producing a crosslinked product comprising reacting (a) an alkenyl silicone, (b) a hydrogen siloxane (c) optionally a cure inhibitor, and (d) a catalyst, optionally in the presence of a solvent, wherein the catalyst comprises a compound of the formula:

Formula (I)

wherein $R^1$—$X^2$—$R^2$ is a diene that is bonded to platinum in an $\eta^4$-mode and is a branched chain, an unbranched chain, a cyclic system, or a bicyclic system having 4 to 30 carbon atoms;

$E^1$ and $E^2$ are independently chosen from monoanionic ligands of O, $NR^3$, a carboxyl group [C(O)O], or S;

$R^3$ is independently hydrogen, or a monovalent hydrocarbon radical having from 1 to 30 carbon atoms;

$X^1$ is a divalent hydrocarbyl group selected from a substituted or unsubstituted alkylene, or arylene group with the proviso that the $E^1$-$X^1$-$E^2$ ligand of Formula (I) does not include ureylene or alpha hydroxy acid ligands;

$X^2$ is a divalent hydrocarbyl selected from a substituted or unsubstituted alkylene, arylene, or cycloalkylene group, whereby the bonding olefin moieties are terminal and/or internal and $X^2$ represents bridges between the olefinic groups; and n is 0, 1, 2, 3, or 4.

2. The process of claim 1, wherein $E^1$ and $E^2$ are O.

3. The process of claim 1, wherein $R^1$—$X^2$—$R^2$ is chosen from 1,5-cyclooctadiene, norbornadiene, dicyclopentadiene, or 1,5-hexadiene.

4. The process of claim 1, wherein $E^1$-$X^1$-$E^2$ is chosen from amidophenolate, phenylenediamide, benzenedithiolate, mercaptophenolate, mercaptoethanolate, pinacolate, ethylene diolate, propandiolate, catecholate, substituted catecholate, salicylate, oxalate, or malonate.

5. The process of claim 4, wherein $R^1$—$X^2$—$R^2$ is 1,5-cyclooctadiene.

6. The process of claim 1, wherein $E^1$-$X^1$-$E^2$ is pinacolate, and $R^1$—$X^2$—$R^2$ is 1,5-cyclooctadiene.

7. The process of claim 1, wherein $E^1$-$X^1$-$E^2$ is represented by the formula:

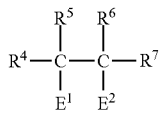

where $R^4$, $R^5$, $R^6$, and $R^7$ are independently chosen from hydrogen, a C1-C20 alkyl, and a C6-C10 aryl.

8. The process of claim 7, wherein $E^1$ and $E^2$ are each O.

9. The process of claim 1, wherein $E^1$-$X^1$-$E^2$ is represented by the formula:

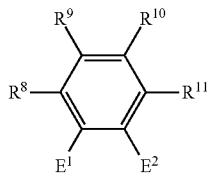

where $R^8$, $R^9$, $R^{10}$, and $R^{11}$ are independently chosen from hydrogen and a C1-C20 alkyl.

10. The process of claim 9, wherein $R^8$, $R^9$, $R^{10}$, and $R^{11}$ are each hydrogen.

11. The process of claim 9, wherein $R^8$ and $R^{10}$ are independently chosen from a C1-C20 alkyl, and $R^9$ and $R^{11}$ are each hydrogen.

12. The process of claim 11, wherein $R^8$ and $R^{10}$ are each tert-butyl.

13. The process of claim 9, wherein $E^1$ and $E^2$ are independently chosen from 0 and S.

14. The process of claim 1, wherein the curable alkenyl silicone is of the formula:

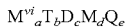

wherein $M^{vi}_a = R^{12}_2R^{13}SiO_{1/2}$, $T_b = R^{14}SiO_{3/2}$ where $R^{14}$ is chosen from $R^{12}$ or $R^{13}$; $D_c = R^{12}R^{14}SiO_{2/2}$ where $R^{14}$ is chosen from $R^{12}$ or $R^{13}$; $M_d = R^{12}_3SiO_{1/2}$; and $Q_e = SiO_{4/2}$; $R^{12}$ is independently selected from a monovalent hydrocarbon radical having one to forty carbon, optionally containing at least one heteroatom; and $R^{13}$ is selected from a terminal olefinic monovalent hydrocarbon radical having two to forty carbon atoms, optionally containing at least one heteroatom, where the composition of the alkenyl silicone comprises at least two unsaturated groups reactive to hydrosilylation per chain; a≥0, b≥0, d≥0, e≥0; and a+b+c+d+e is in the range of 50-20,000.

15. The process of claim 1, wherein the hydrogen siloxane is chosen from a compound of the formula $M_aM^H_bD_{c'}D^H_{d'}T_eT^H_fQ_g$, where the subscripts a', b', c', d', e', f, and g are such that the molar mass of the hydrogen siloxane is between 100 and 100,000 Dalton; M is a monofunctional group of formula $R^{15}_3SiO_{1/2}$, D is a difunctional group of formula $R^{15}_2SiO_{2/2}$, T is a trifunctional group of formula $R^{15}SiO_{3/2}$, and Q is a tetrafunctional group of formula $SiO_{4/2}$, $M^H$ is $HR^{15}_2SiO_{1/2}$, $T^H$ is $HSiO_{3/2}$, and $D^H$ is $R^{15}HSiO_{2/2}$, where each occurrence of $R^{15}$ is independently chosen from a C1-C40 alkyl, a C1-C40 substituted alkyl, a C6-C14 aryl or substituted aryl, wherein $R^{15}$ optionally contains at least one heteroatom.

16. The process of claim 1, wherein the inhibitor is chosen from ethylenically unsaturated amides, aromatically unsaturated amides, acetylenic compounds, ethylenically unsaturated isocyanates, olefinic siloxanes, unsaturated hydrocarbon diesters, unsaturated hydrocarbon mono-esters of unsaturated acids, conjugated or isolated ene-ynes, hydroperoxides, ketones, sulfoxides, amine, phosphines, phosphites, nitriles, diaziridines, or a combination of two or more thereof.

17. The process of claim 1, wherein the concentration of platinum is from about 100 parts per billion (ppb) to about 100 ppm.

18. The process of claim 1, wherein component (c) is present in an amount of from about 0 to about 10 weight percent.

19. The process of claim 1, wherein components (a)-(d) are provided in a single composition.

20. The process of claim 1, wherein the reaction is completed in about 10 seconds or less.

21. The process of claim 1, wherein the reaction is completed in 2-5 seconds.

22. The process of claim 1, wherein the process is conducted by heating at a temperature above room temperature.

23. The process of claim 1, wherein the a composition of components (a)-(d) has a working life of at least 2 hours when the concentration of inhibitor (c) is about 0.25 weight percent or less.

24. A composition comprising (a) an alkenyl silicone, (b) a hydrogen siloxane, (c) optionally a cure inhibitor, and (d) a catalyst, optionally in the presence of a solvent, wherein the catalyst comprises a compound of the formula:

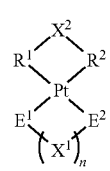

Formula (I)

wherein $R^1$—$X^2$—$R^2$ is a diene that is bonded to platinum in an $\eta^4$-mode and is a branched chain, an unbranched chain, a cyclic system, or a bicyclic system having 4 to 30 carbon atoms;

$E^1$ and $E^2$ are independently chosen from monoanionic ligands of O, $NR^3$, a carboxyl group [C(O)O], or S;

$R^3$ are each independently hydrogen, or a monovalent hydrocarbon radical having from 1 to 30 carbon atoms;

$X^1$ is a divalent hydrocarbyl group selected from a substituted or unsubstituted alkylene, or arylene group with the proviso that the $E^1$-$X^1$-$E^2$ ligand of Formula (I) does not include urelyene or alpha hydroxy acid ligands;

$X^2$ is a divalent hydrocarbyl selected from a substituted or unsubstituted alkylene, arylene, or cycloalkylene group, whereby the bonding olefin moieties are terminal and/or internal and $X^2$ represents bridges between the olefinic groups; and n is 0, 1, 2, 3, or 4.

25. The composition of claim 24, wherein $E^1$ and $E^2$ are 0.

26. The composition of claim 24, wherein $R^1$—$X^2$—$R^2$ is chosen from 1,5-cyclooctadiene, norbornadiene, dicyclopentadiene, or 1,5-hexadiene.

27. The composition of claim 24, wherein $E^1$-$X^1$-$E^2$ is chosen from amidophenolate, phenylenediamide, benzenedithiolate, mercaptophenolate, mercaptoethanolate, pinacolate, ethanediolate, propanediolate, catecholate, substituted catecholate, salicylate, oxalate, or malonate.

28. The composition of claim 27, wherein $R^1$—$X^2$—$R^2$ is 1,5-cyclooctadiene.

29. The composition of claim 24, wherein the catalyst (c) is chosen from pinacolate-Pt-cycloooctadiene; propanediolate-Pt-cyclooctadiene; salicylate-Pt-cyclooctadiene, or a combination of two or more thereof.

30. The composition of claim 24, wherein the curable alkenyl silicone is of the formula:

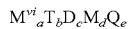

wherein $M^{vi}_a=R^{12}_2R^{13}SiO_{1/2}$; $T_b=R^{14}SiO_{3/2}$ where $R^{14}$ is chosen from $R^{12}$ or $R^{13}$; $D_c=R^{12}R^{14}SiO_{2/2}$ where $R^{14}$ is chosen from $R^{12}$ or $R^{13}$; $M_d=R^{12}_3SiO_{1/2}$; and $Q_e=SiO_{4/2}$; $R^{12}$ is independently selected from a monovalent hydrocarbon radical having one to forty carbon, optionally containing at least one heteroatom; and $R^{13}$ is selected from a terminal olefinic monovalent hydrocarbon radical having two to forty carbon atoms, optionally containing at least one heteroatom, where the alkenyl silicone comprises at least two unsaturated groups reactive to hydrosilylation per chain; a≥0, b≥0, d≥0, e≥0; and a+b+c+d+e is in the range of 50-20,000.

31. The composition of claim 24, wherein the hydrogen siloxane is chosen from a compound of the formula $M_{a'}M^H_{b'}D_{c'}D^H_{d'}T_{e'}T^H_{f'}Q_{g'}$, where the subscripts a', b', c', d', e', f, and g are such that the molar mass of the siloxane-type reactant is between 100 and 100,000 Dalton; M is a monofunctional group of formula $R^{15}_3SiO_{1/2}$, D is a difunctional group of formula $R^{15}_2SiO_{2/2}$, T is a trifunctional group of formula $R^{15}SiO_{3/2}$, and Q is a tetrafunctional group of formula $SiO_{4/2}$, $M^H$ is $HR^{15}_2SiO_{1/2}$, $T^H$ is $HSiO_{3/2}$, and $D^H$ is $R^{15}HSiO_{2/2}$, and each occurrence of $R^{15}$ is independently chosen from a C1-C40 alkyl, a C1-C40 substituted alkyl, a C6-C14 aryl or substituted aryl, wherein $R^{15}$ optionally contains at least one heteroatom.

32. The composition of claim 24, wherein the inhibitor is chosen from ethylenically unsaturated amides, aromatically unsaturated amides, acetylenic compounds, ethylenically unsaturated isocyanates, olefinic siloxanes, unsaturated hydrocarbon diesters, unsaturated hydrocarbon mono-esters of unsaturated acids, conjugated or isolated ene-ynes, hydroperoxides, ketones, sulfoxides, amine, phosphines, phosphites, nitrites, diaziridines, or a combination of two or more thereof.

33. The composition of claim 24, wherein the concentration of platinum is from about 100 parts per billion (ppb) to about 100 ppm.

34. The composition of claim 24, comprising components (a)-(d) as a single component composition.

35. A cured material prepared from the composition of claim 24.

36. A coating formed from the composition of claim 24.

37. A substrate having a surface thereof at least partially coated with the coating of claim 36.

38. The substrate of claim 37, wherein the coating is anchored to the surface of the substrate.

39. A compound of the formula:

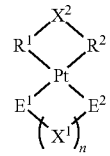

Formula (I)

wherein $R^1$—$X^2$—$R^2$ is a diene that is bonded to platinum in an $\eta^4$-mode and is a branched chain, an unbranched chain, a cyclic system, or a bicyclic system having 4 to 30 carbon atoms;

$E^1$-$(X^1)_n$-$E^2$ is chosen from mercaptophenolate, pinacolate, propanediolate, or salicylate; and $X^2$ is a divalent hydrocarbyl such as substituted or unsubstituted alkylene, arylene, or cycloalkylene group, whereby the bonding olefin moieties are terminal and/or internal and $X^2$ represents bridges between the olefinic groups.

40. The compound of claim 39, wherein $R^1$—$X^2$—$R^2$ is chosen from 1,5-cyclooctadiene, norbornadiene, dicyclopentadiene, or 1,5-hexadiene.

41. The compound of claim 39, wherein the compound is chosen from pinacolate-Pt-cyclooctadiene; propanediolate-Pt-cyclooctadiene; or salicylate-Pt-cyclooctadiene.

* * * * *